US012718678B1

(12) United States Patent
Al-Dossary et al.

(10) Patent No.: US 12,718,678 B1
(45) Date of Patent: Aug. 25, 2026

(54) MODULAR WEARABLE SAFETY DEVICE

(71) Applicant: Saudi Electricity Company, Riyadh (SA)

(72) Inventors: Khalid Al-Dossary, Dammam (SA); Mohammed Bin Rashed, Dammam (SA); Mahmood Almoallem, Dammam (SA); Hassan Alnasser, Dammam (SA)

(73) Assignee: SAUDI ELECTRICITY COMPANY, Riyadh (SA)

( * ) Notice: Subject to any disclaimer, the term of this patent is extended or adjusted under 35 U.S.C. 154(b) by 0 days.

(21) Appl. No.: 19/388,325

(22) Filed: Nov. 13, 2025

(30) Foreign Application Priority Data

Oct. 17, 2025 (SA) ................................ 1020258087

(51) Int. Cl.
*G08B 21/16* (2006.01)
*A61B 5/00* (2006.01)
*A61B 5/024* (2006.01)
*G01N 33/00* (2006.01)

(52) U.S. Cl.
CPC .......... *G08B 21/16* (2013.01); *A61B 5/02438* (2013.01); *A61B 5/681* (2013.01); *A61B 5/742* (2013.01); *A61B 5/7455* (2013.01); *G01N 33/005* (2013.01); *G01N 33/0054* (2013.01); *G01N 33/0057* (2013.01)

(58) Field of Classification Search
CPC ..... G08B 21/16; A61B 5/02438; A61B 5/681; A61B 5/742; A61B 5/7455; G01N 33/005; G01N 33/0054; G01N 33/0057
USPC .......................................................... 340/632
See application file for complete search history.

(56) References Cited

U.S. PATENT DOCUMENTS

2018/0085058 A1* 3/2018 Chakravarthi ......... G16H 40/67
2018/0271442 A1* 9/2018 Dupuy ............... A61B 5/02438
2019/0056766 A1* 2/2019 Mou ..................... G06F 1/1601
2020/0260966 A1* 8/2020 McCalmont ......... A61B 5/6833
2022/0071505 A1* 3/2022 Bosua .................. A61B 5/0507
2022/0361810 A1* 11/2022 Price .................... A61B 5/4833
2024/0188872 A1* 6/2024 Al-Ali .................... A61B 5/256
2024/0201031 A1* 6/2024 Kao ........................ G01L 1/142

* cited by examiner

*Primary Examiner* — Kerri L Mcnally
(74) *Attorney, Agent, or Firm* — MH2 Technology Law Group, LLP

(57) ABSTRACT

A modular, wearable, safety device for monitoring the safety of a wearer and the wearer's environment comprising at least one biometric sensor and a plurality of sensors for measuring environmental data. The sensors are each removably interchangeable with each other. The central processing unit is configured to receive data from the at least one biometric sensor and the plurality of sensors and transmit the received data to the wireless communications module so that the wireless communications module can transmit the received data to an external server or database.

13 Claims, 8 Drawing Sheets

MODULAR WEARABLE SAFETY DEVICE

CROSS REFERENCE TO RELATED APPLICATIONS

This application claims the benefit of U.S. Provisional Application No. SA 1020258087, filed on Oct. 17, 2025, entitled Modular Wearable Safety Device, which is incorporated by reference in its entirety.

FIELD

The present disclosure relates to a modular, wearable, safety device. More particularly, but not exclusively, the present disclosure relates to a modular, wearable, safety device that has a plurality of sensors that are removably interchangeable with each other.

BACKGROUND

Background description includes information that will be useful in understanding the present invention. It is not an admission that any of the information provided herein is prior art or relevant to the presently claimed invention, or that any publication specifically or implicitly referenced is prior art.

Electric power generation and transmission stations or places that operate on petroleum products, usually contain different types of gases. Other environments such as manufacturing facilities or pharmaceutical facilities also contain products that can produce different types of gases that may be harmful to humans.

Being able to detect the level of different harmful gases is helpful to alert people exposed to dangerous levels of gas to remove themselves from the area (such as a carbon monoxide alarm in a domestic environment).

In electric power generation and transmission stations, the emission of toxic gases from equipment and pumps as a result of a certain defects that occur due to the wear and tear of the equipment can cause many deaths and human injuries.

Typical systems use traditional detectors that measure a single type of gas, and alerts users in the area with an alarm. These detectors can only measure a single gas and are unable to assist in analyzing incidents or their effect on the people within the environment.

Other systems have the drawback of being extremely bulky and therefore fixed in place. These systems are unable to detect specific local concentrations of potentially harmful gases around specific people within the environment.

SUMMARY

There is provided, according to a first aspect of the present disclosure, a modular, wearable, safety device for monitoring the safety of a wearer and the wearer's environment. The safety device comprises: a display screen; at least one biometric sensor; and a plurality of connection points. Each connection point of the plurality of connection points comprises a connector, each connector comprising a universal interface. The safety device comprises a plurality of sensors for measuring environmental data, wherein each sensor of the plurality of sensors comprises a common corresponding interface for engaging with the universal interface of the connector. Each sensor of the plurality of sensors is removably connected to its respective connection point of the plurality of connection points via the universal interface and the common corresponding interface, such that each sensor is removably interchangeable with each other. The safety device comprises a wireless communications module and a central processing unit electrically connected to the display screen, the wireless communications module, the at least one biometric sensor, and the plurality of sensors via the plurality of connection points. The central processing unit is configured to receive data from the at least one biometric sensor and the plurality of sensors, and transmit the received data to the wireless communications module so that the wireless communications module can transmit the received data to an external server or database.

Advantageously, the device is wearable. This enables the monitoring of the individual wearers themselves through the biometric sensor, but also enables better monitoring of the individual wearer's direct surrounding environment. This provides a more accurate determination of the safety level of the environment.

Advantageously, each of the sensors are removably interchangeable with each other. This enables the sensors specifically useful for a particular environment to be swapped into the safety device to optimise the gas profile that is being detected by the device.

The plurality of sensors may comprise gas sensors.

The plurality of sensors may be gas sensors.

The plurality of sensors may comprise any combination of: a methane sensor; a carbon monoxide sensor; an ammonia sensor; a carbon dioxide sensor; a hydrogen sensor; a hydrogen sulfide sensor; an oxygen sensor; and/or a sulfur hexafluoride sensor.

The safety device may comprise a temperature sensor.

The safety device may comprise a microphone.

The microphone may record audio and store the audio in a digital storage unit.

This has the benefit of providing more information and context that can be retrieved from the safety device in the aftermath of an accident, for example.

The at least one biometric sensor may comprise one or more of: a heart rate sensor; a blood oxygen sensor; a temperature sensor; a sweat sensor; and/or a galvanic skin response (or skin conductance) sensor.

The central processing unit may comprise a preconfigured set of instructions that enable the central processing unit to analyse the received data, determine whether the wearer or the wearer's environment is safe, and automatically generate an alert if either the wearer or the wearer's environment is not safe.

This has the advantage of being able to locally determine the safety of the wearer and the wearer's environment, while not exclusively relying on external transmissions.

The alert may be transmitted to the external server via the wireless communications module.

The alert may comprise a request for emergency assistance.

The external server may comprise a dashboard for monitoring all of the devices.

The alert may be displayed to the wearer on the display screen.

The alert may comprise first-aid instructions. The alert may comprise instruction to the wearer to leave the environment.

The safety device may comprise a vibrator. The alert may comprise activating the vibrator to alert the wearer.

The safety device may be a watch comprising a flexible strap and a fixation element for fixing to the flexible strap, such that the watch can be secured to a wrist of the wearer.

The wireless communications module may have a wireless range of greater than 6 kilometres.

The wireless communications module may be capable of communicating with a wireless communications module of another safety device, thereby extending the effective range of the device.

The safety device may comprise a digital storage unit electrically connected to the central processing unit. The digital storage unit may be configured to record historic biometric and environmental data generated by the at least one biometric sensor and the plurality of sensors.

The digital storage unit may comprise a waterproof casing.

The safety device may comprise a waterproof housing.

The safety device may be assigned to a specific wearer. The central processing unit may receive health records corresponding to the specific wearer, such that the central processing unit analyses the received data in combination with the health records corresponding to the specific wearer, to provide a more accurate and context-aware alerting mechanism.

The safety device may comprise a filter for preventing particulates from entering the safety device.

The filter may comprise a metallic grid that enhances robustness while allowing gas to enter the safety device.

There is provided, according to a second aspect of the present disclosure, a method of monitoring the safety of a wearer and the wearer's environment using a modular, wearable, safety device. The method comprises: selecting a plurality of sensors for measuring environmental data, the selection being at least partly a function of the wearer's environment; removably attaching each sensor of the plurality of sensors to a respective connection point of a plurality of connection points comprised in the safety device, each connection point comprising a connector having a universal interface, and each sensor comprising a common corresponding interface for engaging with the universal interface of the connector; such that each sensor is removably interchangeable with each other; measuring environmental data using the plurality of sensors; measuring biometric data using a biometric sensor; receiving the environmental data and the biometric data at a central processing unit; transmitting the environmental data and the biometric data to a wireless communications module; and transmitting the environmental data and the biometric data to an external server or database.

The method may comprise: analysing the received environmental data and biometric data at the central processing unit; determining whether the wearer or the wearer's environment is safe; and automatically generating an alert if either the wearer or the wearer's environment is not safe.

The method may comprise: removing a sensor of the plurality of sensors from its connection point of the safety device, and removably attaching a different sensor to the same connection point of the safety device.

There is provided, according to a third aspect of the present disclosure, a safety system, the safety system comprising: a plurality of modular, wearable, safety devices according to the first aspect, each safety device in wireless communication with a remote server; and a platform that receives and displays data transmitted from each of the safety devices.

The plurality of safety devices may wirelessly communicate with each other as part of a mesh network.

It will be appreciated that features disclosed in relation to one aspect of the present disclosure may be applicable to another aspect of the present disclosure, and vice versa.

BRIEF DESCRIPTION OF THE DRAWINGS

The manner in which the above-recited features of the present invention is understood in detail, a more particular description of the invention, briefly summarized above, may be had by reference to embodiments, some of which are illustrated in the appended drawings. It is to be noted, however, that the appended drawings illustrate only typical embodiments of the present disclosure and are therefore not to be considered limiting of its scope, for the present disclosure may admit to other equally effective embodiments.

The foregoing and other objects, features and advantages of the present invention, as well as the invention itself, will be more fully understood from the following description of preferred embodiments, when read together with the accompanying drawings.

DETAILED DESCRIPTION

The present disclosure relates to the field of modular, wearable, safety devices, and more particularly to modular, wearable safety devices with interchangeable gas sensors.

The principles of the present invention and their advantages are best understood by referring to FIG. 1 to FIG. 7D. In the following detailed description of illustrative or exemplary embodiments of the disclosure, specific embodiments in which the disclosure may be practiced are described in sufficient detail to enable those skilled in the art to practice the disclosed embodiments. The following detailed description is, therefore, not to be taken in a limiting sense, and the scope of the present disclosure is defined by the appended claims and equivalents thereof. References within the specification to "one embodiment," "an embodiment," "embodiments," or "one or more embodiments" are intended to indicate that a particular feature, structure, or characteristic described in connection with the embodiment is included in at least one embodiment of the present disclosure.

Figure 1:
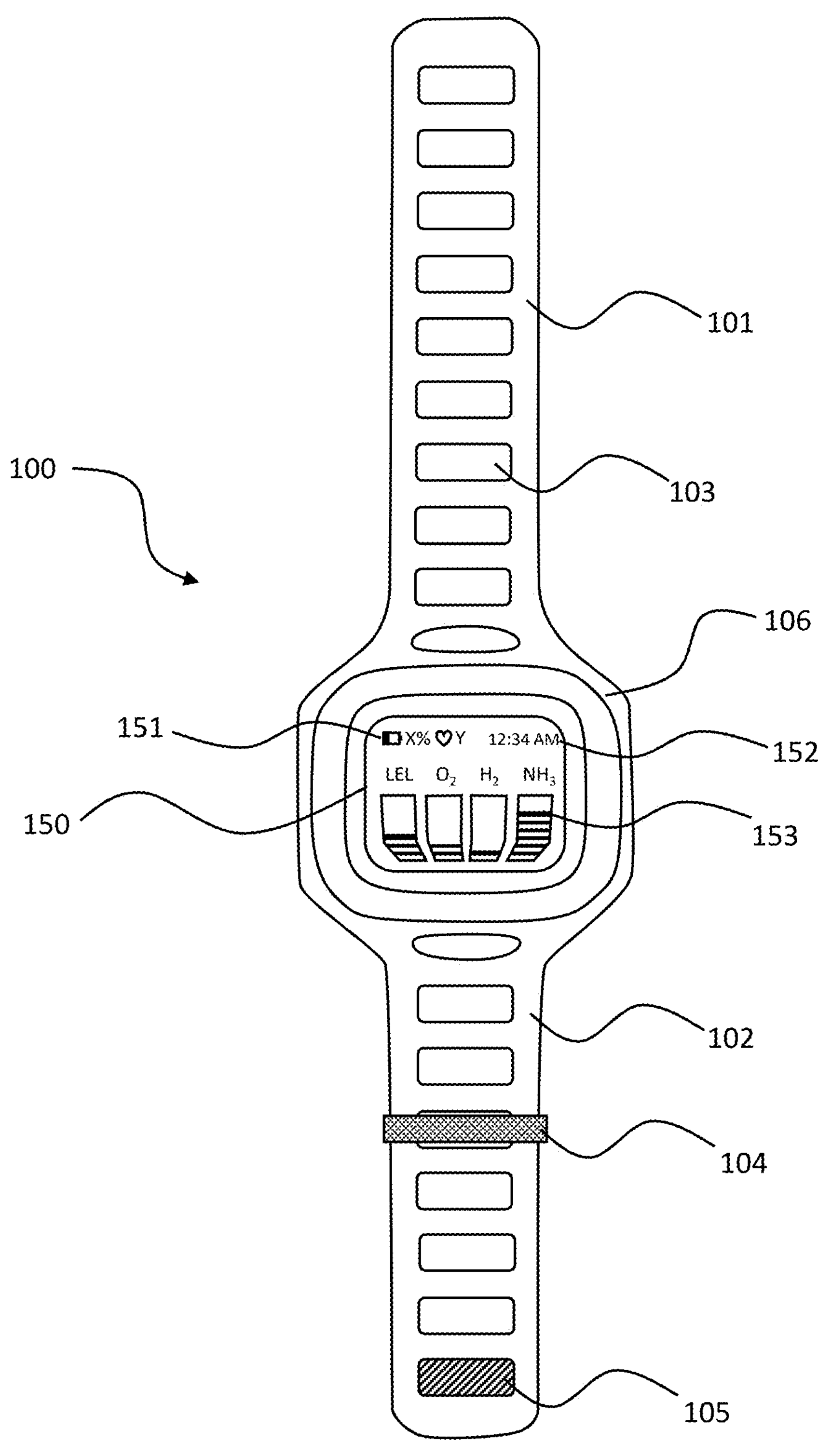
FIG. 1 shows a modular, wearable, safety device according to an embodiment of the present disclosure.

FIG. 1 shows a modular, wearable, safety device 100 according to an embodiment of the present disclosure.

The safety device 100 is a watch 100. The safety device 100 has a pair of straps 101, 102 that secure the main body 106 of the safety device 100 to a wrist of the wearer. Each of the straps 101, 102, have a plurality of openings 103 that enable a clasp 105 to be receivably engaged therein to secure the watch 100 to the wearer, with a variable length adjustment. The strap 102 has a band 104 to secure the trailing end of the other strap 103, preventing it from loosely flapping when worn.

The main body 106 comprises a digital screen 150. The screen 150 displays information to the wearer. In this embodiment, the watch has been fitted with ammonia, hydrogen, and oxygen sensors.

The digital screen 150 display the level of ammonia, hydrogen, and oxygen 153 in the environment. The onboard central processing unit of the device also computes a lower explosive limit based on the combination of gases that it is detecting, which is also displayed to the wearer.

Also provided are user data and general information 151 which includes the wearer's heartrate, the battery level of the watch, the signal strength of the watch, and the time.

In embodiments, the watch is suitable for use in a plurality of different environments. The sensors can be chosen to be tailored to the specific environment in question. For example, the watch can be configured for and is suitable for use in petrochemical factories, oil reservoirs, mines, power generation plants, gas factories, and medicine/pharmaceutical plants/factories.

In embodiments, the device comprises a predictive AI component. The predictive AI component is part of the monitoring system that anticipates physical stress, issuing alerts before fatigue sets in. It tracks vital signs, including temperature, heart pulse, and blood oxygen saturation, preventing potential work accidents before they occur.

Figure 2A:
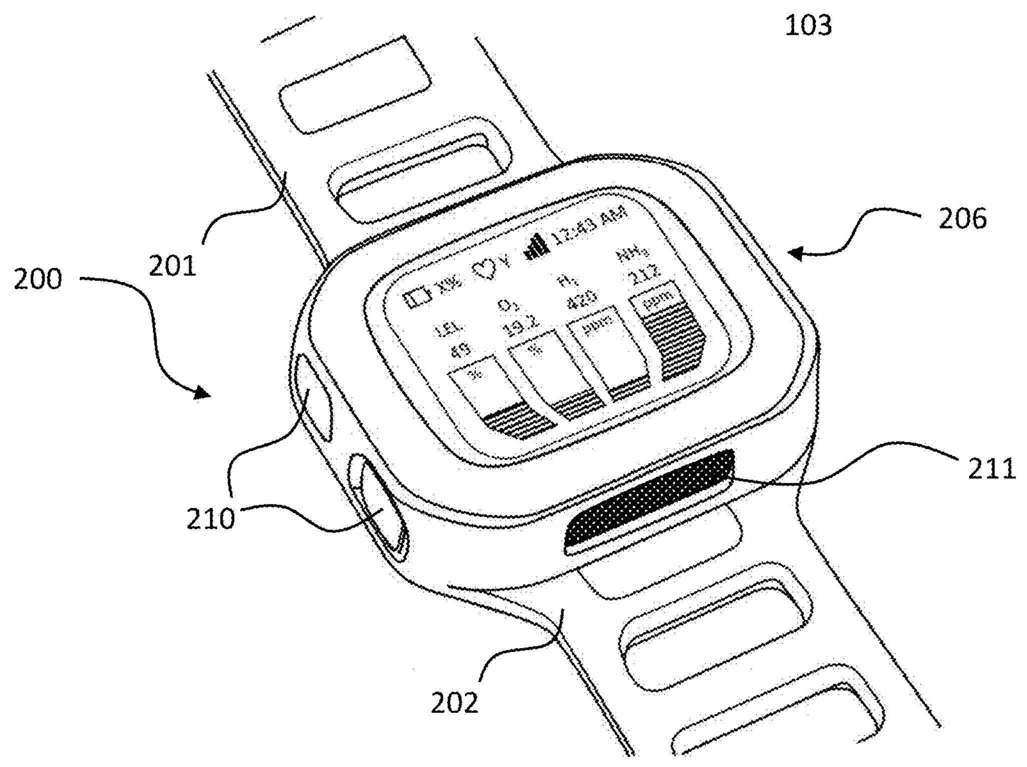
FIG. 2A shows a perspective view of a modular, wearable, safety device according to an embodiment of the present disclosure.

FIG. 2A shows a perspective view of a modular, wearable, safety device 200 according to an embodiment of the present disclosure.

The safety device has a main body 206, similar to the main body 106 of FIG. 1. The information displayed on the screen of the main body 206 is similar to that of FIG. 1 and will not be repeated for conciseness.

On the side of the main body 206 are provided a pair of buttons 210. The buttons are waterproof.

In embodiments, the buttons may be customizable. In embodiments, one of the buttons is a power button for turning on the device. In embodiments, one of the buttons is an alert button. In embodiments, one of the buttons is a menu button.

Also provided in the main body 206 is a mesh 211, that enables gas to permeate into the main body 206 while preventing larger particulates such as dust from entering.

In embodiments, the mesh 211 is fine enough to prevent low pressure water (such as from splashes or brief submersion) from entering into the main body 206.

Figure 2B:
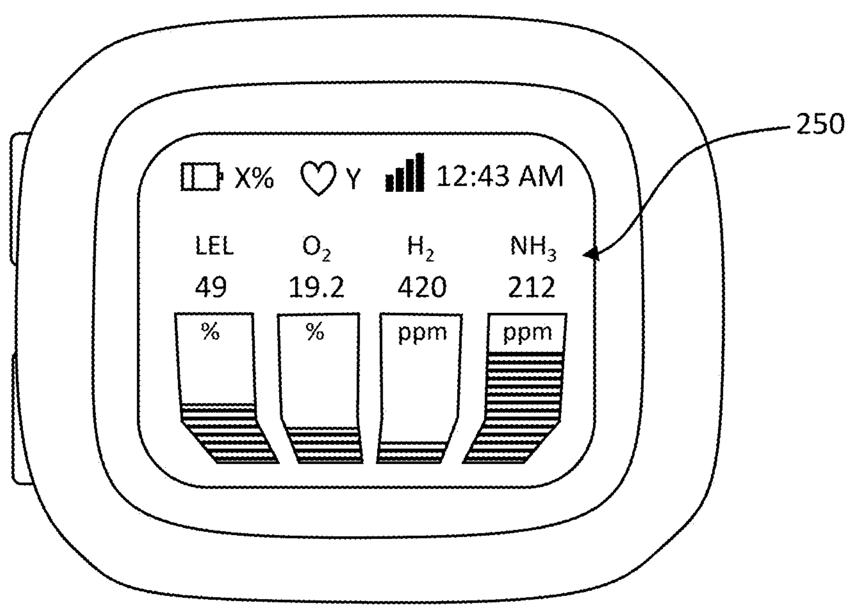
FIG. 2B shows a screen of a modular, wearable, safety device according to an embodiment of the present disclosure.

FIG. 2B shows a screen 250 of a modular, wearable, safety device 200 according to an embodiment of the present disclosure.

The screen 250 displays data corresponding to the sensors that have been removably connected to the device 200 when the device was initially set up for the corresponding environment.

In this exemplary embodiment, the data shows LEL (lower explosive limit), oxygen concentration, hydrogen concentration, and ammonia concentration. The concentrations are shown either as a percentage (for abundant gases such as oxygen) or in ppm (parts per million) for less abundant concentrations where precise knowledge of exact parts per volume of gas is important for the determination of safety of the environment.

The screen 250 also displays the battery level of the watch 200, the heart rate of the wearer, the signal strength of the watch, and the local time.

In embodiments, the screen also displays other biometric data that is being captured by the watch, such as stress or temperature, for example.

Figure 3:
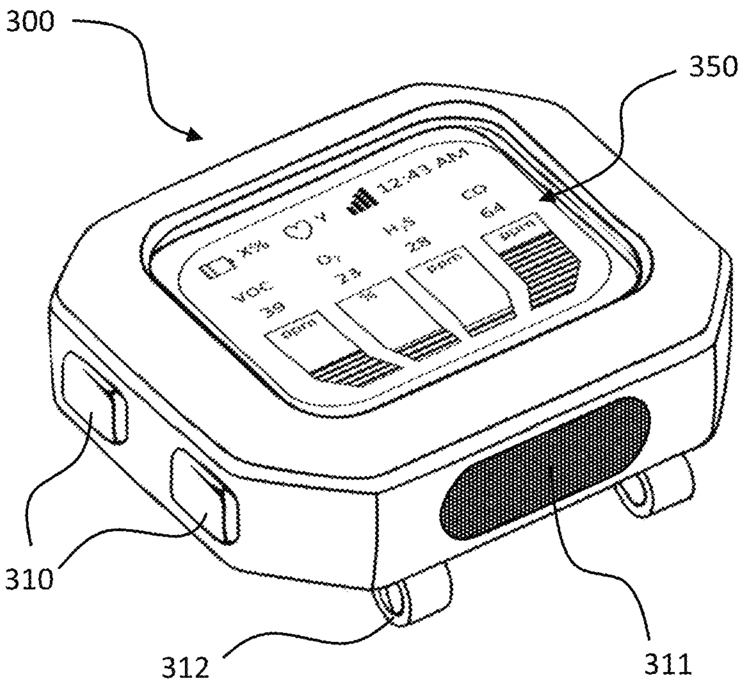
FIG. 3 shows a perspective view of a modular, wearable, safety device according to an embodiment of the present disclosure.

FIG. 3 shows a perspective view of a modular, wearable, safety device 300 according to an embodiment of the present disclosure.

For the avoidance of duplication of information, it will be appreciated that like reference numerals denote similar elements. For example, the pair of buttons 310 are similar to the pair of buttons 210 of FIG. 2. Likewise, the mesh 311 is similar to the mesh 211 of FIG. 2.

The screen 350 shows similar data to the screen 250. In this embodiment, different sensors having been used, resulting in the display of different data. Here, the concentration of VOC (volatile organic compounds), oxygen, hydrogen sulfide, and carbon monoxide are displayed to the wearer.

It will be appreciated that while this information is being displayed to the wearer, the information is also being transmitted via a wireless communications module from the watch 300 to a remote server where information from a plurality of similar safety devices is collected and arranged to provide a holistic overview of the safety of an overall environment and the safety of all of the wearers.

The main body also comprises a pair of loops 312. The loops 312 enable the removable connection of straps to the main body.

In embodiments, the device is not worn as a watch, and instead is worn on the persons clothing via clips or a clasp, which may be attached to the pair of loops 312 instead of a strap.

Figure 4:
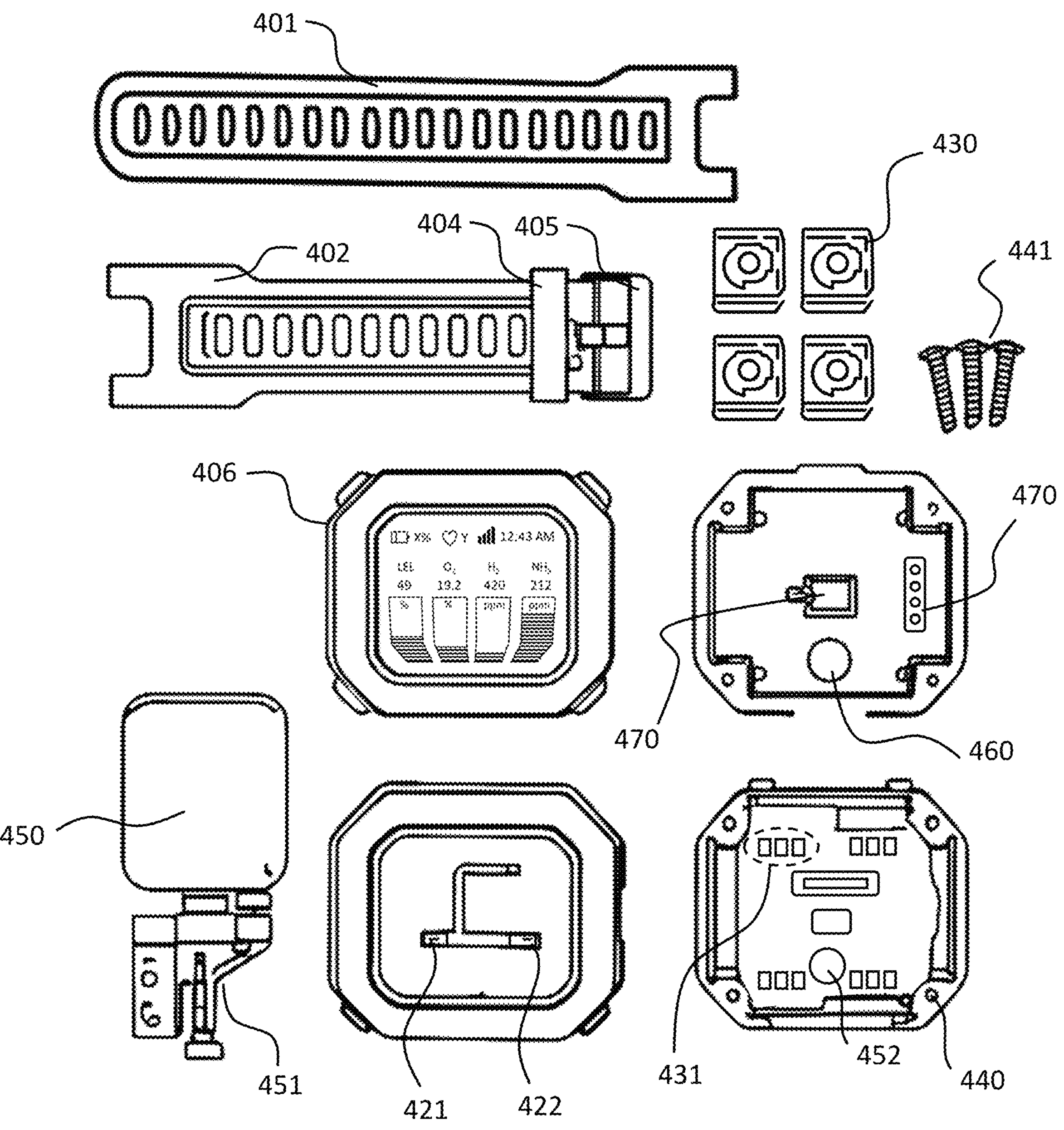
FIG. 4 shows a deconstructed modular, wearable, safety device according to an embodiment of the present disclosure.

FIG. 4 shows a deconstructed modular, wearable, safety device according to an embodiment of the present disclosure.

A main body 406 is shown, which is similar to the main bodies of FIGS. 1, 2 and 3.

A pair of straps 401, 402 is shown. In this embodiment, a buckle-type clasp 405 is used to secure the free ends of the straps 401, 402 when connected to the main body 406, with the loop 404 being used to secure the free end of the strap 401 when connected to the clasp 405.

The screen 450 is also shown separate from the main body 406. The screen 450 is connected to a circuit-board 451 that is connected to a central processing unit 452. The central processing unit 452 sends instructions to the screen to control the display output. The central processing unit is pre-programmed with algorithms that enable the central processing unit to analyze data that is received from the various sensors provided in the device, to accurately determine the safety of the wearer and the environment.

An exhaustion sensor comprises two metal parts 421, 422 installed on the device that are configured to be in contact with the wearer's body in order to read the effect of physical exhaustion through measurement of conductance of the wearer's skin.

Screws 441 are provided to secure the device together through threaded holes 440.

A battery 460 provides power to the device.

A plurality of different gas sensors 430 are provided, of which any number can be chosen for the appropriate environment in which the wearer will be operating.

Four universal connection points 431 are provided that enable any of the sensors 430 to be connected to any of the four connection points 431, thereby enabling full modularity and customization of the functionality of the device dependent on the wearer and their environment.

On the underside, a heart rate sensor 470 is provided. In embodiments, the heart rate sensor doubles as a blood oxygen concentration sensor.

A recharging port 470 is provided to enable the wearer to recharge the battery 460 when the battery 460 level is indicated to be low.

In embodiments, one of the sensors is an accelerometer. The accelerometer may provide fall down detection in combination with an on-board GPS, thereby providing a smart fall and slip detection algorithm that can instant alert for nearby workers and rescue centers, ensuring swift assistance and medical support if required.

Figure 5:
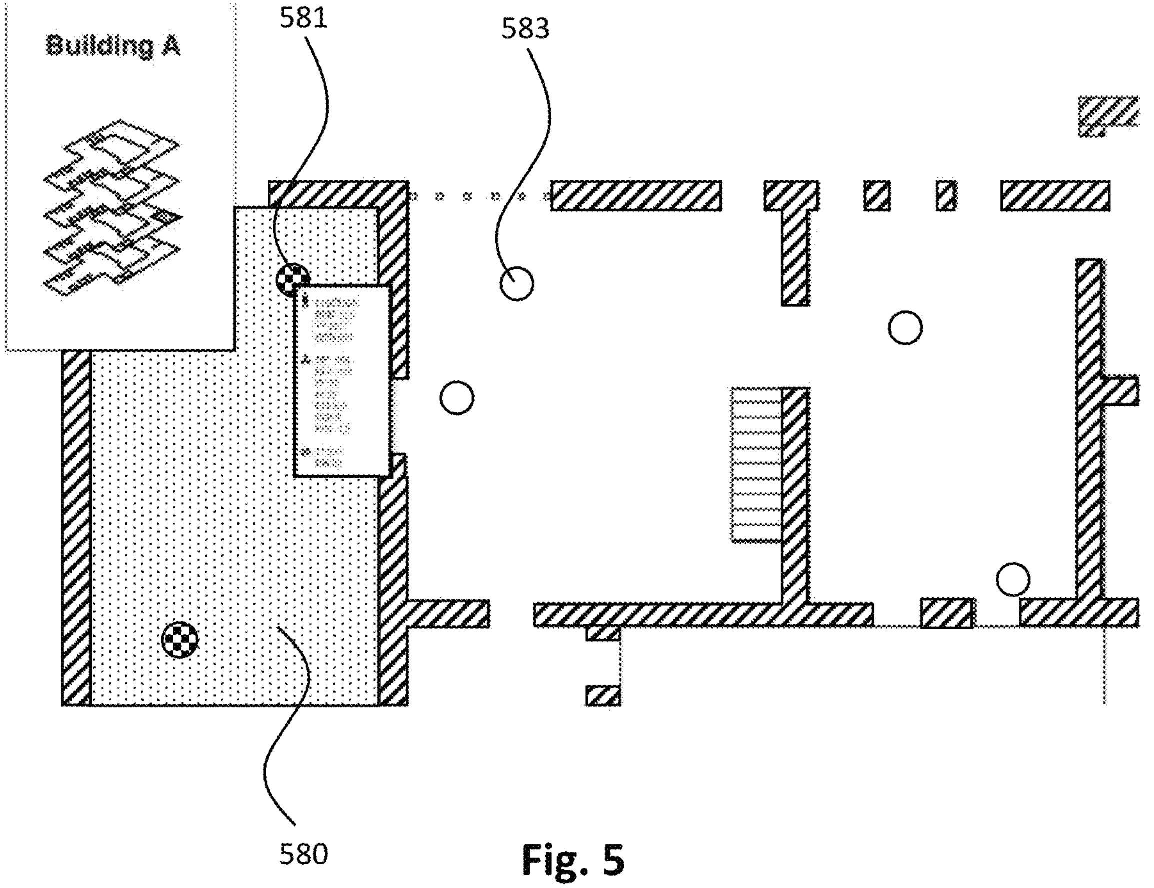
FIG. 5 shows a dashboard view of an environment according to an embodiment of the present disclosure.

FIG. 5 shows a dashboard view of an environment according to an embodiment of the present disclosure. In embodiments, the devices are internet of things (IoT) based.

The dashboard shows a tracking and alert system of gases that are measured from each of the devices worn by each of the wearers, and the system also includes a supervisor page (this map-like overview) and a personal page (see FIG. 6) for each user in which all the data extracted from the sensors are clarified and statistics related to the work done on a daily basis are provided. It also provides information that can be used to raise safety performance and reduce work expenses by determining the time spent in the work of any field, and the system also allows the improvement of the environment of field sites.

Here, the device of a user 581 has determined that the levels of gas detected around that user are above the safe limit. This is demonstrated on the dashboard by highlighting the user and providing a readout of all of the data captured by the device in real-time. Additionally, the dashboard identifies the area that the wearer is in 580 and designates it as unsafe. For this reason, other users within the same area are also highlighted as potentially being in an unsafe environment.

Wearers in a separate room 583 are providing data within safe levels, so the system identifies that their respective area is safe to be in and does not highlight either the wearer or the area as being potentially unsafe.

In embodiments, the system of the dashboard autonomously dispatches a rescue command to the facility's emergency center, providing real-time accident location data, along with comprehensive historical and current gas readings as well as the user's vital signs and First Aid instructions.

Figure 6:
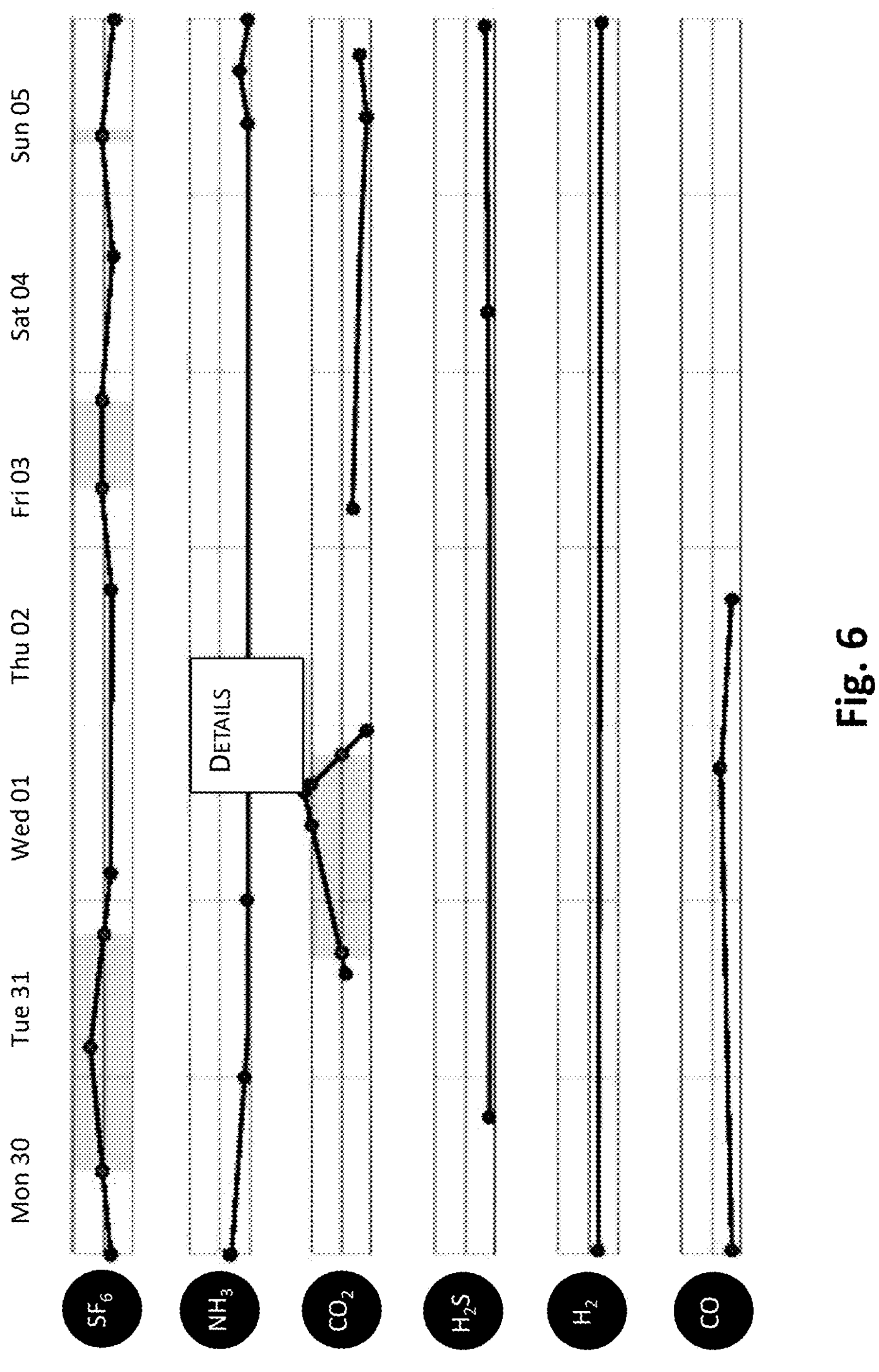
FIG. 6 shows a dashboard view of a dataset for a modular, wearable, safety device according to an embodiment of the present disclosure.

FIG. 6 shows a dashboard view of a dataset for a modular, wearable, safety device according to an embodiment of the present disclosure.

The dashboard shows the readout of the detection of various gases for a specific wearer during a one-week period. Times during which the level of gas was elevated above safe levels are highlighted for potential investigation. Times in which the level of gas was elevated far beyond the safe levels are further highlighted with a call-out and additional details surrounding the incident for further investigation.

The device also helps predict the malfunction of some devices by sensing various gases. The invention also tracks the user's location accurately via satellite, in addition to that the device provides the necessary information to investigate in the event of an accident by storing sounds in addition to all the other information captured by the various sensors. All information from the scene is stored inside a fireproof and waterproof storage unit. The device alerts the wearer immediately after the gas ratios change from the expected limit in the work environment, and in the event that the user does not respond to the alert, the device communicates with a rescuer or remote server who is previously identified automatically and sends all the registered information as follows: the location of the incident; time and date of the incident; proportions and concentration of all gases; heart rate; the extent of physical exhaustion; and audio recording two minutes before and after the incident.

In embodiments, the device comprises a high-speed processor that facilitates the rapid and complex analysis of multiple critical parameters. This includes the real-time correlation of wearer's health records, current physiological vital signs, and ambient gas concentration levels. This sophisticated analytical capability enables highly accurate and context-aware alerting mechanisms tailored to individual worker profiles and immediate environmental hazards.

Figure 7A:
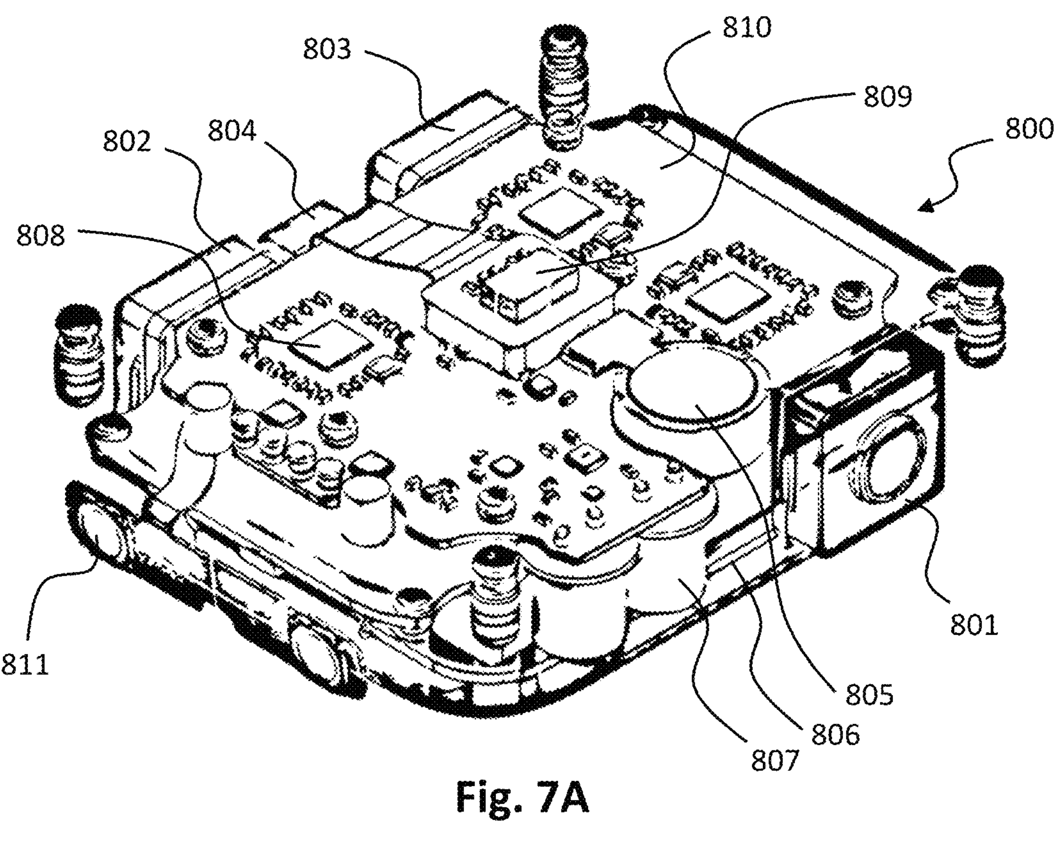
FIGS. 7A-D show internal views of a modular, wearable, safety device according to an embodiment of the present disclosure.

FIG. 7A shows a bottom perspective view of a modular, wearable, safety device according to an embodiment of the present disclosure.

The bottom view shows the bottom side of the device 800, which is the side that would be in contact with the wrist of the wearer of the device, when in use.

The device is equipped with three gas sensors 801, 802, 803. These gas sensors may be interchangeable with other gas sensors for detection of other gases. It can be seen that the gas sensors 801, 802, 803 are all of the same form factor, meaning that interchangeability of the gas sensors is achievable within the device, which enhances the safety and useability of the device in different environmental scenarios.

A buzzer 804 is also provided on the device 800. The buzzer 804 makes an alarm or sound to alert the wearer that the risk has increased, or that the level of one or more gases being senses is approaching dangerous levels.

Similarly, a vibration motor 805 is included in the device to provide an alternative means of alerting the wearer that the level of one or more of the gases being senses is at or approaching dangerous levels. In some environments, the environment will be very loud, masking the sound from the buzzer 804. In such scenarios, the vibration motor 805 provides haptic feedback to the wearer, causing them to look at the device 800, thereby noticing the levels of the detected gases in the room or environment.

An antenna 806 is included to enable the device to wirelessly communicate. The wireless communication may be 5G, or Wi-Fi, for example.

A lower explosive limit (LEL) sensor 807 detects whether the level of certain gases is approaching the point that could cause an explosion if it were to be ignited with a spark (for example).

The interface circuit and integrated circuit chips 808 are shown on the motherboard 810.

Two buttons 811 are provided to allow the user to interact with the device 800. The buttons 811 are electrically connected to the circuit chips 808 on the motherboard 810.

Figure 7B:
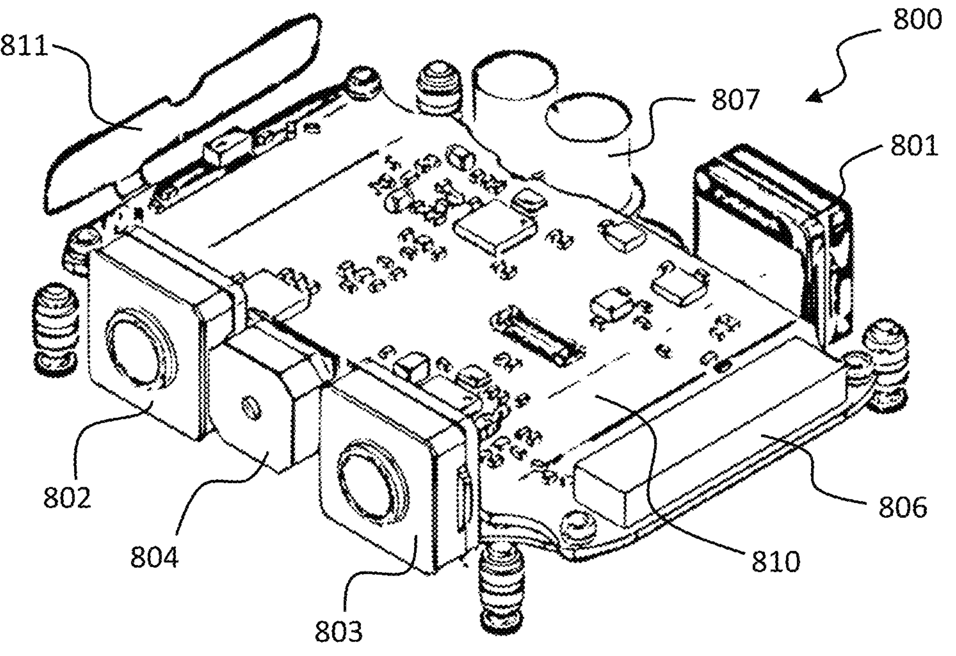

FIG. 7B shows a top perspective view of a modular, wearable, safety device according to an embodiment of the present disclosure.

The top perspective view shows the side of the device that would be facing outwards, away from the wearer, when in use on the wearer's wrist, for example.

Like reference numerals have been used to denote similar elements with respect to FIG. 7A, therefore, those will not be described again in relation to FIG. 7B.

Since the top view is the outward facing side, it needs to be configured to enable space for the battery and screen. As seen in the figure, the gas sensors 801, 802, 803 protrude upwards from the motherboard 810, defining a space in which a battery and screen can fit at least partially within.

Figure 7C:
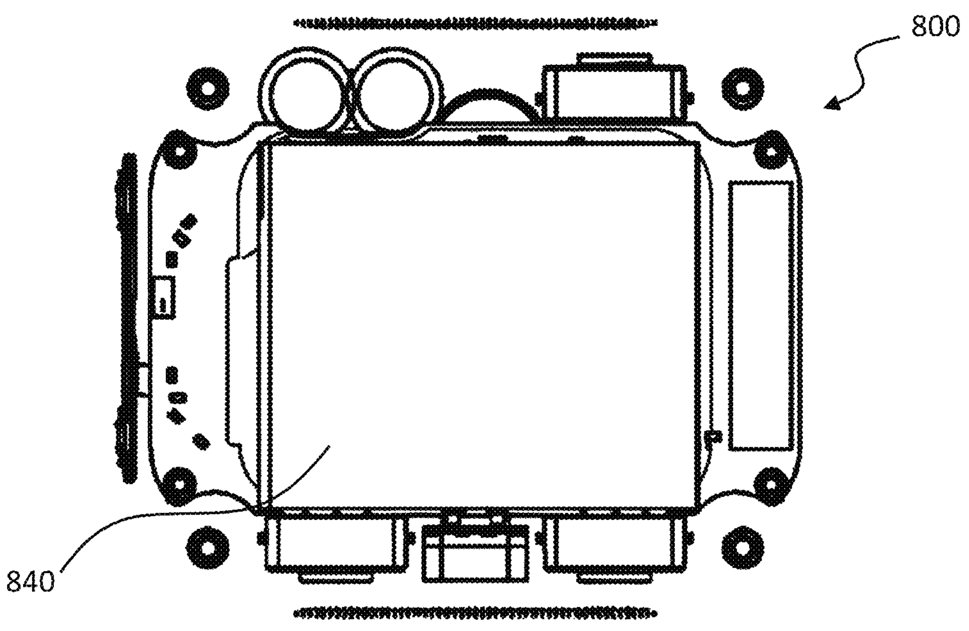

FIG. 7C shows a top view of a modular, wearable, safety device 800 according to an embodiment of the present disclosure. This figure shows a battery 840 having been installed on the device.

Figure 7D:
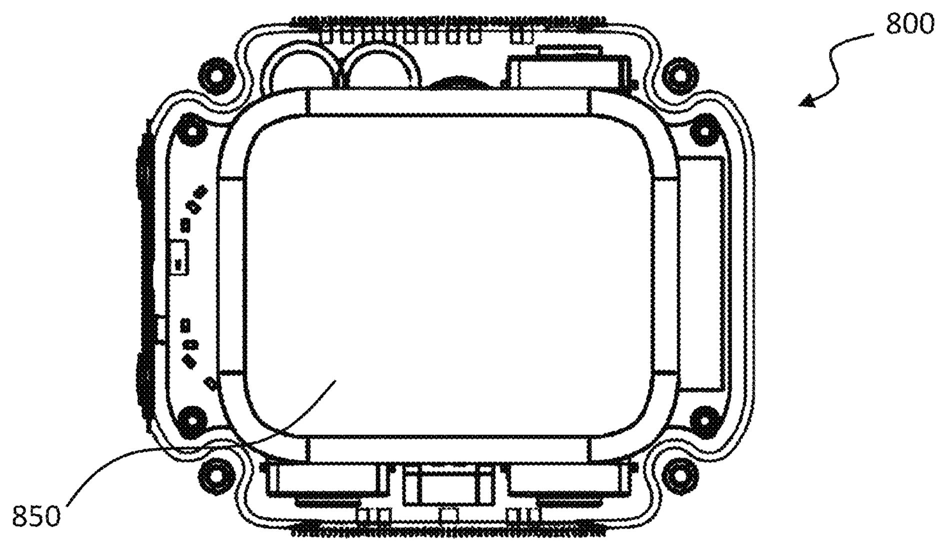

FIG. 7D shows a top view of a modular, wearable, safety device 800 according to an embodiment of the present disclosure. This figure builds upon FIG. 7C, and shows the screen 850 further installed on top, being the most outward facing portion of the wearable device.

Embodiments and exemplary features of embodiments of the present disclosure not described in relation to specific figures presented herein, shall now be described. It will be appreciated that features described in accordance with these embodiments of the present disclosure may be applicable to other embodiments of the present disclosure, such as those described in relation to one or more figures, for example.

In embodiments, an electronic board connects all sensors (including gas sensors and LEL sensors) and electronic units, in addition to some resistors and capacitors, to ensure the operation and delivery of all electronic signals being sent and received by the respective sensors to and from the central electronic board. In embodiments, a digital electronic processor is installed on the central electronic board. In embodiments, the processor receives and sends information to and from all sensors and electronic units. In embodiments, the processor comprises algorithms that are programmed to analyze all information quickly and effectively to assess the safety of the individual and the safety of the environment, to avoid an accident. For example, the processer may receive signals from a plurality of sensors corresponding to differing concentrations of different gases/particulates/vapors in the environment. The processor may calculate that that composition of gases/particulates/vapors is approaching or above a recommended safe level and generate a warning signal that is transmitted back to a central controller or server. In embodiments, each of the components individually may not be sufficient to trigger a warning signal; however, the processer may be able to determine a safe level for a mixture of different components in the atmosphere that may otherwise not trigger an alarm for a single sensor device.

In embodiments, there is also provided a storage unit installed on the central electronic board which, connected with the digital processor, stores all historical biometric and environmental information. The storage unit may be able to retrieve the data and enable the processor or an external computing apparatus to analyze the data after an incident has occurred. In embodiments, there is also provided a wireless communication unit installed on the central electronic board and connected to the digital processor, where it is used as a link between this smart device and a tracking and alerting system on a remote computer or server designed to monitor a plurality of the smart devices in an area or facility (see FIG. 5, for example). In embodiments, there is a location unit that also facilitates this functionality, whereby the location unit determines the wearer's location and speed through satellite positioning (GPS). The location unit may be characterized by high accuracy and transmits the information in real-time to the digital processor to analyze, store and send the information to the remote server or computer.

In embodiments, a time and date identification and storage unit is also installed on the central electronic board. The time and date identification and storage unit may identify and logs both time and date. This unit may comprise a small battery that helps to preserve information in the event of a power outage from the overall device. The date and time identification and storage unit may be connected to the digital processor by I2C technology.

In embodiments, a temperature sensor is provided under the display. The temperature sensor may be installed on the central electronic board and linked to the digital processor. The temperature sensor may play a significant role in determining the ambient temperature level of the work environment and alerting the wearer or remote server if the temperature rises or falls from normal levels. In embodiments, algorithms programmed within the digital processor also work to analyze the temperature and alert the wearer in time to ensure the wearer has enough time to exit or move away to a safe place.

In embodiments there is also provided an acceleration sensor. In embodiments, the acceleration sensor is installed near the digital processor on the central electronic board and linked with the digital processor. The acceleration sensor may help in sensing the fall or rolling of the wearer for any reason. The acceleration sensor may also be used to calculate the number of steps taken by the wearer whereby the processor stores them and sends them to a remote database to be analyzed.

The digital processor may be integrated circuit chips.

In embodiments, the device measures many different gases using electronic sensors, such as an oxygen gas sensor, which is installed or electrically connected to the central electronic board/motherboard and linked to the digital processor (which may be integrated circuit chips). In the example of an oxygen gas sensor, this sensor helps monitor the level of oxygen gas concentration in the work area so that the wearer is alerted when oxygen gas is less than normal according to the algorithms that are programmed in the digital processor (or integrated circuit chips). In embodiments, the device may comprise one or more of a combination of a carbon dioxide sensor, a carbon monoxide sensor, an ammonia sensor, a hydrogen gas sensor, a butane gas sensor, a hydrogen sulfide gas sensor, and a sulfur hexafluoride gas sensor, or any alternative sensor. These one or more sensors may be installed on the central electronic board and linked to the digital processor where it monitors the level of gas concentration in the work area until the wearer is alerted when the level of one or more gases individually or in combination rises above the permissible limit according to the algorithms that are programmed in the digital processor.

A universal serial port (USB) may be used to charge a battery. In embodiments, the device also contains a heart rate sensor that is installed on the central electronic board and linked to the digital processor by (I2C) technology. The measurement of the heartrate helps in tracking the extent of the impact of a potential gas leakage on the wearer and also provides an indication of the extent of physical fatigue of the wearer as a result of the potential gas leakage. The processor, through this heartrate sensor, may analyze the data and alert the wearer or a critical party (such as emergency responders or the remote server) if necessary. In embodiments, the device comprises an exhaustion sensor. In embodiments, the exhaustion sensor comprises two metal parts installed on the device from the outside to be in contact with the wearer's body in order to read the effect of physical exhaustion through measurement of conductance. This sensor may also be linked with the digital processor to analyze the information according to the algorithms programmed within the processor, and thus the wearer is alerted to take a break or inform the critical party in the event of extreme fatigue or fainting. In embodiments, a vibrator is installed on the central electronic board and linked to the digital processor, where it is activated to alert the wearer of an alarm so that the wearer can exit in time or seek necessary assistance.

In embodiments, the device also contains a microphone installed on the central electronic board. The microphone may be linked to the digital processor. The microphone may send audio data to the processor to be stored in the storage unit and sent to the remote server or database in the event of an incident. The microphone may provide audio details about the incident, through which the details of the incident can be identified so that appropriate measures can be taken to avoid similar incidents in the future.

It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents. The disclosures and the description herein are intended to be illustrative and are not in any sense limiting the present disclosure, defined in scope by the following claims.

Many changes, modifications, variations and other uses and applications of the present disclosure will become apparent to those skilled in the art after considering this specification and the accompanying drawings, which disclose the preferred embodiments thereof. All such changes, modifications, variations and other uses and applications, which do not depart from the spirit and scope of the present disclosure, are deemed to be covered by the invention, which is to be limited only by the claims which follow.

The invention claimed is:

1. A modular, wearable, safety device for monitoring the safety of a wearer and the wearer's environment, the safety device comprising:

a display screen;

at least one biometric sensor;

a plurality of connection points;

wherein each connection point of the plurality of connection points comprises a connector, each connector comprising a universal interface;

a plurality of sensors for measuring environmental data;

wherein each sensor of the plurality of sensors comprises a common corresponding interface for engaging with the universal interface of the connector;

wherein each sensor of the plurality of sensors is removably connected to its respective connection point of the plurality of connection points via the universal interface and the common corresponding interface, such that each sensor is removably interchangeable with each other;

a wireless communications module;

a central processing unit electrically connected to the display screen, the wireless communications module, the at least one biometric sensor, and the plurality of sensors via the plurality of connection points; and a filter for preventing particulates from entering the safety device;

wherein the central processing unit is configured to receive data from the at least one biometric sensor and the plurality of sensors, and transmit the received data to the wireless communications module so that the wireless communications module can transmit the received data to an external server or database; and wherein the filter comprises a metallic grid that enhances robustness while allowing gas to enter the safety device.

2. The modular, wearable, safety device as claimed in claim 1, wherein the central processing unit comprises a preconfigured set of instructions that enable the central processing unit to analyse the received data, determine whether the wearer or the wearer's environment is safe, and automatically generate an alert if either the wearer or the wearer's environment is not safe.

3. The modular, wearable, safety device as claimed in claim 2, wherein the alert is transmitted to the external server via the wireless communications module.

4. The modular, wearable, safety device as claimed in claim 2, wherein the alert is displayed to the wearer on the display screen.

5. The modular, wearable, safety device as claimed in claim 2, wherein the safety device comprises a vibrator, and wherein the alert comprises activating the vibrator to alert the wearer.

6. The modular, wearable, safety device as claimed in claim 1, wherein the safety device is a watch comprising a flexible strap and a fixation element for fixing to the flexible strap, such that the watch can be secured to a wrist of the wearer.

7. The modular, wearable, safety device as claimed in claim 1, wherein the wireless communications module has a wireless range of greater than 6 kilometres.

8. The modular, wearable, safety device as claimed in claim 1, wherein the safety device comprises a digital storage unit electrically connected to the central processing unit; wherein the digital storage unit is configured to record historic biometric and environmental data generated by the at least one biometric sensor and the plurality of sensors.

9. The modular, wearable, safety device as claimed in claim 8, wherein the digital storage unit comprises a waterproof casing.

10. The modular, wearable, safety device as claimed in claim 1, wherein the safety device is assigned to a specific wearer, wherein the central processing unit receives health records corresponding to the specific wearer, such that the central processing unit analyses the received data in combination with the health records corresponding to the specific wearer, to provide a more accurate and context-aware alerting mechanism.

11. A method of monitoring the safety of a wearer and the wearer's environment using a modular, wearable, safety device, the method comprising:

selecting a plurality of sensors for measuring environmental data, the selection being at least partly a function of the wearer's environment;

removably attaching each sensor of the plurality of sensors to a respective connection point of a plurality of connection points comprised in the safety device, each connection point comprising a connector having a universal interface, and each sensor comprising a common corresponding interface for engaging with the universal interface of the connector, such that each sensor is removably interchangeable with each other;

measuring environmental data using the plurality of sensors;

filtering using a metallic mesh, the metallic mesh preventing particulates from entering the safety device while enhancing robustness and allowing gas to enter the safety device;

measuring biometric data using a biometric sensor;

receiving the environmental data and the biometric data at a central processing unit;

transmitting the environmental data and the biometric data to a wireless communications module; and transmitting the environmental data and the biometric data to an external server or database.

12. The method according to claim 11, wherein the method comprises:

analysing the received environmental data and biometric data at the central processing unit;

determining whether the wearer or the wearer's environment is safe; and automatically generating an alert if either the wearer or the wearer's environment is not safe.

13. The method according to claim 11, wherein the method comprises:

removing a sensor of the plurality of sensors from its connection point of the safety device;

removably attaching a different sensor to the same connection point of the safety device.

* * * * *